United States Patent [19]

Sugimoto

[11] 4,419,395

[45] Dec. 6, 1983

[54] PERFUMED PENDANT

[76] Inventor: Terutaka Sugimoto, 2-20-1 Nakazato, Kita-Ku, Tokyo, Japan

[21] Appl. No.: 409,101

[22] Filed: Aug. 18, 1982

[51] Int. Cl.³ .......................... A44C 25/00; A61L 9/04
[52] U.S. Cl. ........................................ 428/28; 239/36; 239/56; 428/905
[58] Field of Search .................... 428/28, 79, 905, 15, 428/40; 239/34, 36, 56, 60

[56] References Cited

U.S. PATENT DOCUMENTS

| | | | |
|---|---|---|---|
| 3,334,586 | 8/1967 | Jaffa et al. | 428/909 X |
| 3,784,102 | 1/1974 | Stults | 428/28 X |
| 4,160,685 | 7/1979 | Kuroda | 428/79 X |

FOREIGN PATENT DOCUMENTS 1329309  9/1973  United Kingdom ............... 428/905

Primary Examiner—Henry F. Epstein
Attorney, Agent, or Firm—Wenderoth, Lind & Ponack

[57] ABSTRACT

A perfumed pendant which has a three-dimensional configuration and comprises a front vinyl sheet having a design printed thereon, a back vinyl sheet having a design mating with the design on the front vinyl sheet printed thereon and welded at the outer peripheral edge thereof to the outer peripheral edge of the front vinyl sheet, a foam resilient padding interposed between the front and back vinyl sheets to give the three-dimensional configuration to the pendant and a capsulated perfume layer laminated to the outer surface of the front vinyl sheet at a selected area of the front vinyl sheet outer surface.

13 Claims, 5 Drawing Figures

FIG.1 FIG.2
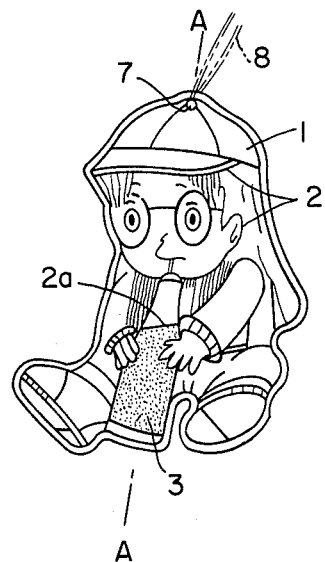
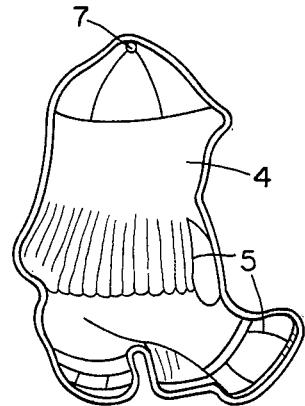
FIG.3 FIG.4 FIG.5
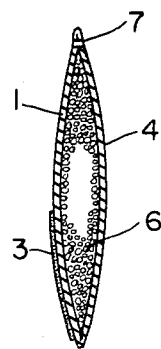
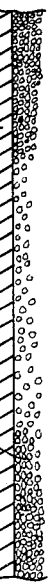
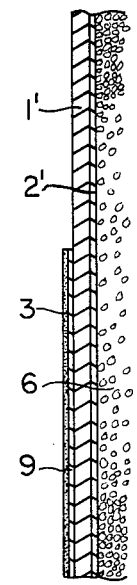

PERFUMED PENDANT

BACKGROUND OF THE INVENTION

This invention relates to a perfumed ornament such as a perfumed pendant which comprises front and back vinyl sheets welded together at their outer peripheral edges with a foam padding such as foam urethane or sponge rubber interposed therebetween and having designs printed thereon and a capsulated perfume layer laminated to the outer surface of the front vinyl sheet and having a design printed on the outer surface of the layer.

Of late, ornaments such as brooches and pendants, synthetic resin films, paper stickers have been increasingly impregnated with perfume so that such articles can be used not only as ornamentally appreciative articles, but also as fragrant articles. However, such perfume-impregnated ornaments have the disadvantages that they are not acceptable to infants as toys and that they are expensive. And since perfume-impregnated synthetic resin films and paper stickers are flat, they have the disadvantages that the external appearance of such articles is inevitably monotonous and insipid, that they are not pleasant to the touch and that they are not suitable for being carried about.

SUMMARY OF THE INVENTION

Therefore, the present invention is to eliminate the disadvantages inherent in the prior art perfume-impregnated ornaments such as brooches and pendants, perfume-impregnated synthetic resin films and perfume-impregnated paper stickers as referred to hereinabove and for the purpose, the present invention provides a perfumed pendant which comprises front and back vinyl sheets having designs printed thereon and welded at the outer peripheral edges thereof, a foam resilient padding such as foam synthetic resin interposed between the front and back vinyl sheets and a capsulated perfume layer laminated to the outer surface of the front vinyl sheet at a selected are thereof.

According to one aspect of the present invention, there has been provided a perfumed pendant which comprises a front vinyl sheet having a design printed thereon, a back vinyl sheet having a design mating with said design on the front vinyl sheet printed thereon and welded at the outer peripheral edge thereof to the outer peripheral edge of said front vinyl sheet, a foam resilient padding interposed between said front and back vinyl sheets and a capsulated perfume layer laminated to the outer surface of said front vinyl sheet at a selected area of the front sheet outer surface.

According to another aspect of the present invention, there has been provided a perfumed pendant which comprises a front transparent lustrous vinyl sheet having a design printed on the inner surface thereof, a back vinyl sheet having a design mating with said design on the front vinyl sheet printed on the outer surface thereof and welded at the outer peripheral edge thereof to the outer peripheral edge of said front vinyl sheet, a foam resilient padding interposed between said front and back vinyl sheets, an undercoating of transparent ink for vinyl applied to the outer surface of said front vinyl sheet at a selected area thereof, and a capsulated perfume layer laminated to said undercoating.

The above and other objects, features and attendant advantages of the present invention will be more readily apparent to those skilled in the art from a reading of the following detailed description in conjunction with the accompanying drawing which shows preferred embodiments of the invention for illustration purpose only, but not for limiting the scope of the same in any way.

BRIEF DESCRIPTION OF THE DRAWING

The accompanying drawing shows preferred embodiments of the perfumed pendant according to the present invention in which:

FIG. 1 is a front view of a first embodiment of said perfumed pendant;

FIG. 2 is a back view of said perfumed pendant as shown in FIG. 1;

FIG. 3 is a vertically sectional view taken substantially along the line A—A of FIG. 1;

FIG. 4 is a fragmentary vertically sectional view on an enlarged scale of the embodiment of said perfumed pendant as shown in FIGS. 1 to 3 inclusive; and FIG. 5 is similar to FIG. 4, but shows a modified embodiment of the perfumed pendant.

DETAILED DESCRIPTION OF PREFERRED EMBODIMENTS

The present invention will be now described referring to the accompanying drawing and more particularly, to FIGS. 1 to 4 inclusive in which the first embodiment of the perfumed pendant according to the present invention is shown.

The perfumed pendant generally comprises a front vinyl sheet 1 having a design 2 which represents a figure or animal (the front part of an infant is shown in FIG. 1) printed on one or the outer surface thereof, a capsulated perfume layer 3 laminated to the printed surface 2 of the front vinyl sheet 1 at 2a thereof with a suitable binder (not shown) by a screen printing process and having a design printed on the outer surface thereof (the design is shown as being a bottled refreshing drink in FIG. 1), a back vinyl sheet 4 having a design 5 which mates with the design 2 (the design 5 is shown as being the back part of the infant in FIG. 2) printed on one or the outer surface and welded at the outer peripheral edge thereof to the outer peripheral edge of the front vinyl sheet 1 and a foam resilient padding 6 formed of foam urethane or sponge rubber interposed between the front and back vinyl sheets 1 and 4 to give a three-dimensional configuration to the resulting perfumed pendant. A through hole 7 is formed in the front and back vinyl sheets 1 and 4 at the tops thereof and a string 8 is passed through the hole 7 so that the pendant can be hung on an apparel or the like.

The capsulated perfume layer 3 comprises a plurality of capsules formed of high molecular compound and each containing a predetermined amount of perfume therein and connected together by means of a suitable binder which also serves to secure the capsulated perfume layer 3 to the front vinyl sheet 1. The perfume to be capsulated should be selected depending upon the design printed on the capsulated perfume layer 3, that is, the perfume should be that emitting the scent of the drink represented by the design printed on the capsulated perfume layer 3.

Referring now to FIG. 5 of the accompanying drawing in which a modification of the perfumed pendant as shown in FIGS. 1 to 4 inclusive is illustrated, the modified perfumed pendant is substantially similar to the preceding embodiment except for the front vinyl sheet, the capsulated perfume layer and the provision of an undercoating on the outer surface of the front vinyl sheet. In the embodiment of FIG. 5, the front vinyl sheet 1' is formed of a transparent lustrous vinyl sheet and has a design 2' containing the representation of the bottled drink printed on the inner surface thereof so that the design 2' can be seen on the outer surfaces of the front sheet and capsulated perfume layer through the vinyl sheet and perfume layer as a lustrous design. In the modified embodiment, since the outer surface of the front vinyl sheet 1' is lustrous and the printing ink of the design 2' is not present on the vinyl sheet surface, the capsulated perfume layer 3 can not be easily laminated to the vinyl sheet 1'. Thus, in the modified embodiment, an undercoating 9 of transparent ink compatible with vinyl is applied to the outer surface of the front vinyl sheet 1' at a selected area thereof where the capsulated perfume layer 3 is to be laminated and the capsulated perfume layer 3 which is transparent and has no design printed thereon is then applied to the undercoating 9 by the screen printing process.

It should be understood that in the production of the perfumed pendant of the present invention, the blank vinyl sheets of which the front and back vinyl sheets 1 or 1' and 2 are formed should have dimensions larger than those of the design areas 2 or 2' and 4, respectively and the blank vinyl sheets are superimposed with the padding 6 interposed therebetween and cut along the contours of the design areas 2 or 2' and 4, respectively, by a high frequency welder, for example.

As mentioned hereinabove, since the padding 6 of foam urethane or sponge rubber is interposed between the vinyl sheets 1 or 1' and 4, the resulting entire perfumed pendant is a decorative article having a three-dimensional appearance and a resiliency and the lamination of the capsulated perfume layer on the outer surface of the front sheet 1 or 1' is a novel feature of the present invention. Although the perfume normally does not emit its fragrant scent because it is capsulated, when a portion of the capsulated perfume layer 3 is rubbed or scratched by a human finger nail or tip, the capsule or capsules which are present in the rubbed or scratched portion of the capsulated perfume layer 3 tear and the perfume contained in such torn capsule or capsules emits its fragrant scent.

Thus, according to the present invention, a mentioned hereinabove, since the capsulated perfume is that having the same scent as that peculiar to the refreshing drink or fruit represented by the design printed on the capsulated perfume layer 3 on the front vinyl sheet 1, the perfume contained in the torn capsule or capsules emits the very scent represented by the design on the capsulated perfume layer 3. Furthermore, since the resilient padding 6 is interposed between the front and back vinyl sheets 1 or 1' and 4, the vinyl sheets 1 or 1' and 4 are caused to bulge outwardly or away from each other so that a human finger can positively access to the capsulated perfume layer 3 and gives a moderately resilient touch to the pendant so that a human finger or nail tip can closely contact the capsulated perfume layer 3 and thus, even an infant can use the pendant without difficulties.

By passing the string 8 through the through hole 7 in the pendant, the pendant can be hung on a bag, satchel or apparel and carried about so that the user can smell the scent of the perfume at his desired time and place. Alternatively, the pendant can be hung on a stationary support structure such as a wall, pillar or the like and even in such a case the user's nostril can access to the capsulated perfume layer 3 easily. Lastly, even after all the capsules have been torn and accordingly, all of the perfume has disappeared, since the external appearance of the pendant remains unchanged, the pendant can be still used as a practical ornamental article.

In the foregoing, description has been made of only two embodiments of the present invention, but it will be readily occur to those skilled in the art that the same are illustrative in nature, but do not limit the scope of the invention in any way. The scope of the invention is only limited by the appended claims.

What is claimed is:

1. A perfumed pendant suitable for use by infants comprising a front vinyl sheet having a design printed thereon, a back vinyl sheet having a design mating with said design on the front vinyl sheet printed thereon and welded at the outer peripheral edge thereof to the outer peripheral edge of said front vinyl sheet, a foam resilient padding interposed between said front and back vinyl sheets and a capsulated perfume layer laminated to the outer surface of said front vinyl sheet at a selected area of the sheet outer surface, said front and back sheets bulging outwardly.

2. The perfumed pendant as set forth in claim 1, in which said front and back vinyl sheets have said designs printed on the outer surfaces thereof.

3. The perfumed pendant as set forth in claim 1 or 2, in which said design printed on the front vinyl sheet is the front part of a figure and said design on the back vinyl sheet is the back part of said figure.

4. The perfumed pendant as set forth in claim 1, in which said foam resilient padding is foam urethane rubber.

5. The perfumed pendant as set forth in claim 1, in which said foam resilient padding is foam sponge rubber.

6. The perfumed pendant as set forth in claim 1, in which said capsulated perfume layer comprises a plurality of capsules containing perfume therein and connected together and secured to said front vinyl sheet by means of binder.

7. The perfumed pendant as set forth in claim 1, in which said capsulated perfume layer has a design representing a bottled refreshing drink printed thereon.

8. A perfumed pendant suitable for use by infants comprising a front transparent lustrous vinyl sheet having a design printed on the inner surface thereof, a back vinyl sheet having a design mating with said design on the front vinyl sheet printed on the outer surface thereof and welded at the outer peripheral edge to the outer peripheral edge of said front vinyl sheet, a foam resilient padding interposed between said front and back vinyl sheets, an undercoating of transparent ink applied to the outer surface of said front vinyl sheet at a selected area thereof, and a capsulated perfume layer applied to said undercoating, said front and back sheets bulging outwardly.

9. The perfumed pendant as set forth in claim 8, in which said design on the front vinyl sheet is the front part of a figure and said design on the back vinyl sheet is the back part of said figure.

10. The perfumed pendant as set forth in claim 8, in which said foam resilient padding is foam urethane rubber.

11. The perfumed pendant as set forth in claim 8, in which said foam resilient padding is foam sponge rubber.

12. The perfumed pendant as set forth in claim 8, in which said capsulated perfume layer comprises a plurality of capsules containing perfume therein and connected together and secured to said undercoating by means of binder.

13. The perfumed pendant as set forth in claim 8, in which said capsulated perfume layer has a design representing a bottled refreshing drink printed thereon.

* * * * *